(12) United States Patent
Kieser

(10) Patent No.: US 10,342,664 B2
(45) Date of Patent: *Jul. 9, 2019

(54) STRUCTURALLY ENCODED IMPLANT ALIGNMENT DEVICE AND ENCODING METHOD

(71) Applicant: SEMD HOLDINGS, LLC, San Antonio, TX (US)

(72) Inventor: Brian Kieser, San Antonio, TX (US)

(*) Notice: Subject to any disclaimer, the term of this patent is extended or adjusted under 35 U.S.C. 154(b) by 260 days.

This patent is subject to a terminal disclaimer.

(21) Appl. No.: 15/235,914

(22) Filed: Aug. 12, 2016

(65) Prior Publication Data

US 2017/0095335 A1 Apr. 6, 2017

Related U.S. Application Data

(60) Provisional application No. 62/204,233, filed on Aug. 12, 2015.

(51) Int. Cl.
| | | |
|---|---|---|
| *A61F 2/44* | (2006.01) | |
| *A61F 2/30* | (2006.01) | |
| *A61B 90/94* | (2016.01) | |
| *A61B 90/98* | (2016.01) | |
| *A61B 5/055* | (2006.01) | |
| *A61B 6/03* | (2006.01) | |
| *A61B 8/08* | (2006.01) | |
| *A61B 90/00* | (2016.01) | |

(52) U.S. Cl.
CPC .............. *A61F 2/30* (2013.01); *A61B 5/055* (2013.01); *A61B 6/032* (2013.01); *A61B 6/037* (2013.01); *A61B 8/0841* (2013.01); *A61B 90/94* (2016.02); *A61B 90/98* (2016.02); *A61F 2/44* (2013.01); *A61F 2/442* (2013.01); *A61F 2/4455* (2013.01); *A61B 2090/3916* (2016.02); *A61B 2090/3925* (2016.02); *A61B 2090/3954* (2016.02); *A61B 2090/3966* (2016.02); *A61F 2002/3008* (2013.01); *A61F 2002/3071* (2013.01); *A61F 2002/30617* (2013.01)

(58) Field of Classification Search
CPC .... A61F 2/30; A61F 2/442; A61F 2002/3008; A61B 90/94; A61B 90/98; A61B 5/055; A61B 6/032; A61B 6/037; A61B 8/0841; A61B 2090/3916; A61B 2090/3925; A61B 2090/3954; A61B 2090/3966
USPC ........................ 623/17.11, 17.16; 606/246
See application file for complete search history.

(56) References Cited

U.S. PATENT DOCUMENTS

| | | | |
|---|---|---|---|
| 9,101,321 B1* | 8/2015 | Kieser | ............... A61B 17/7004 |
| 9,424,503 B2* | 8/2016 | Kieser | ............. G06K 19/06046 |
| 9,675,273 B2* | 6/2017 | Gluncic | ............... A61B 5/066 |
| 2011/0160558 A1 | 6/2011 | Rassatt et al. | |
| 2013/0053680 A1 | 2/2013 | Frey | |
| 2013/0105577 A1 | 5/2013 | Hildreth et al. | |
| 2015/0232921 A1 | 8/2015 | Kieser | |

(Continued)

*Primary Examiner* — Pedro Philogene
*Assistant Examiner* — David C Comstock
(74) *Attorney, Agent, or Firm* — Buckingham, Doolittle & Burroughs, LLC

(57) ABSTRACT

An implant device identifiable after implantation is provided. The implant device includes a spinal interbody implant including an implant body including at least one orientation marker rod. Each of the at least one orientation marker rod has a series of physical encodings discernible by an imaging system. The physical encodings encode a respective set of data.

19 Claims, 22 Drawing Sheets

(56) References Cited

U.S. PATENT DOCUMENTS

2017/0000581 A1\* 1/2017 Tokuda .................. A61B 90/39
2017/0209068 A1\* 7/2017 Dyer ...................... A61B 5/055

\* cited by examiner

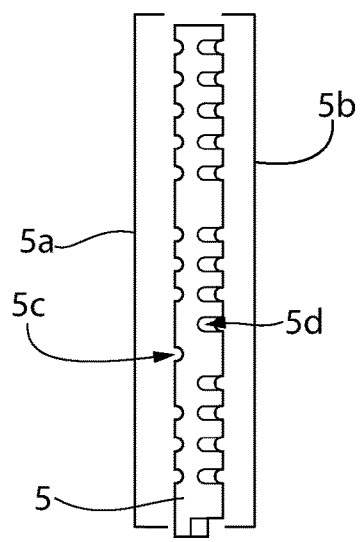
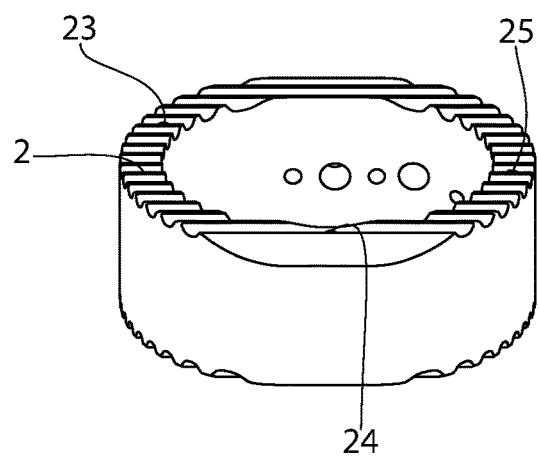
FIG. 11A  FIG. 11B
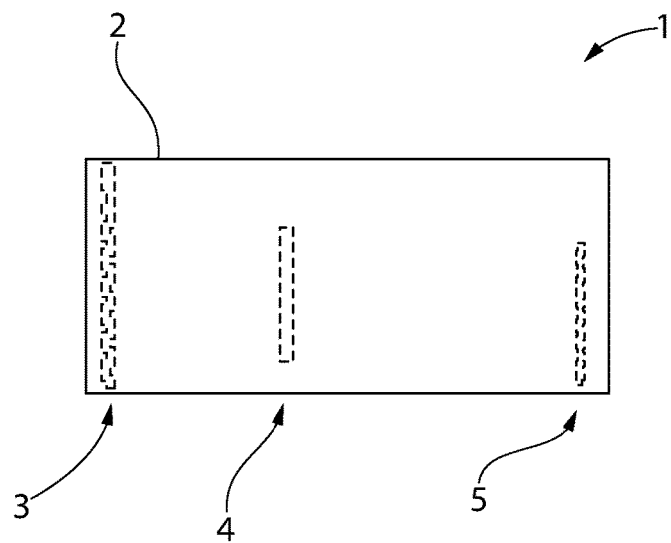
FIG. 11C

Encoding Scheme 1 - Encode Implant
Information in Sets of Notches

Pin 14a

Pin 14b and 14c $3^0 \quad 3^1 \quad 3^2 \quad 3^3 \quad 3^4 \quad 3^5 \quad 3^6 \quad 3^7 \quad 3^8 \quad 3^9$ Lot and Serial Numbers Pattern Code - $1*4^0+3*4^1+0*4^2+2*4^3=1+12+0+128=141$
Base 4 Example - Two Sides, Same Depth Pattern Code - $1*4^0+3*4^1+0*4^2+2*4^3=1+12+0+128=141$
Base 4 Example - One Side, Three Depths Pattern Code - $1*4^0+3*4^1+0*4^2+2*4^3=1+12+0+128=141$
Base 4 Example - One Side, Three Widths Base 9 Encoding Strategy with Possible Notches - Two Sides, Two Depths

STRUCTURALLY ENCODED IMPLANT ALIGNMENT DEVICE AND ENCODING METHOD

RELATED APPLICATION DATA

This application claims the priority benefit of U.S. Provisional Application Ser. No. 62/204,233, filed Aug. 12, 2015, which is hereby incorporated in its entirety herein by reference.

FIELD OF THE INVENTION

The present invention relates to identifiable spinal implants and, in particular, structurally encoded interbody spinal implant assemblies.

BACKGROUND OF THE INVENTION

Medical implant devices used in surgical procedures can be associated with particular information to guide medical professionals before and after the surgical procedure. Each implant device or its packaging carries a wealth of information that is valuable to the surgeon, patient, hospital, the implant manufacturer, medical researchers, healthcare professionals, and medical facilities. However, the information, which may include the implant manufacturer and manufacturer's lot number, the date and location of surgical implantation, the responsible surgeon, any medical notes, photographs, or diagrams relating to the implant, surgery, or condition, may not be adequate, properly recorded, or readily accessible for beneficial use by a healthcare professional, implant manufacturer, or medical researcher after implantation. Problems relating to poor implant records can lead to unnecessary delay or even medical error by healthcare professionals. Moreover, there are many different implant identification methods currently in place instead of a common system to allow manufacturers, distributors, and healthcare facilities and professionals to effectively track, identify, and manage implant devices and medical device recalls. The U.S. Food and Drug Administration recently announced a program focusing on requirements for unique device identifiers for every medical implant device to address the need for a more robust implant device identification system, the details of which are hereby incorporated by reference herein: www.fda.gov/udi.

The present invention is an improvement upon the technology described in U.S. applications Ser. Nos. 14/302,133, 14/302,171, 14/302,197, 14/456,665 and 14/822,613, which are hereby incorporated in their entirety by reference herein.

SUMMARY OF THE INVENTION

In accordance with an aspect of the invention, an implant device identifiable and readable after implantation is provided comprising an implant comprising an implant body, the implant body comprising at least one readable element or a plurality of readable elements, such as one or more orientation marker rods, each of the readable elements having a surface (such as the longitudinal surface of an orientation marker rod) having a series of physical encodings, artifacts or variances, such as notches or indentations discernible by an imaging system, and wherein the physical encodings encode a respective set of data relating to the implant body. While the invention may be described and understood in the context of a spinal interbody implant with imaging-detectable orientation marker rods, it may be applied to any implanted body and any such readable elements of any shape or material, especially those where orientation markers are used to place and assess the positioning of the implant.

The orientation of the orientation marker rods within the implant may be varied in accordance with such factors as the implant type, its intended function, its positioning within the patient, and the desired angle with respect to the implant from which data-acquiring imaging is conducted. Accordingly, the orientation marker rods may be substantially parallel to one another, or perpendicular, or otherwise placed in any desired orientation with respect to one or more of one another based upon such application factors.

It will be appreciated that the orientation marker rods may be of varied geometry or cross-section as may be amenable to encoding sets of data relating to the implant body, procedure or patient. The encoded surface accordingly may be flat, curved or otherwise vary in geometry or cross-section (such as with circular, polygonal or varying cross-section) while still allowing the encoded data to be discerned therefrom.

The physical encodings (such as notches or indentations) discernible by an imaging system may include a plurality of modifications to at least one surface of the readable element or a plurality of readable elements disposed within the readable portion such that the indicia are discernible by any medical imaging modality, such as at least one of x-ray, fluoroscopy, computed tomography, electromagnetic radiation, ultrasound, positron emission tomography (PET) and magnetic resonance imaging.

The orientation marker rods may comprise a readable element, such as a radiopaque element, and having physical encodings disposed on at least one surface or multiple surfaces thereof or disposed within the implant. The surfaces may be any surface of the readable element that permits the encoded data to be read therefrom. In one embodiment, each of the orientation marker rods has physical encodings that encode respective different sets of data relating to the implant body. In another variant embodiment of the invention described herein, each of the orientation marker rods has physical encodings that respectively encode at least two sets of data relating to the implant body.

For instance, the encoding may be placed on sets of opposing sides of a rectangular cross-section, square cross-section or circular cross-section rod; or on multiple arcs of a circular rod (such as on 6 radial 60 degree arcs that could be read from 3 different lateral orientations). In most cases, the data will be read from the three dimensional rod two dimensionally from one or more angles.

Such data may include any data relating to the patient, the patient's medical history, relevant surgical procedure(s) data (including the implant procedure(s)) and/or to the implant body itself, such as information selected from the group consisting of implant type, implant manufacturer identification, implant serial number, implant type and size, implant lot number, a unique device identifier (UDI), data relating to the FDA Global Unique Device Identification Database (GUDID), any other data related to the FDA UDI, or any other encoding related to uniquely identifying the implant body.

In another variant embodiment of the invention described herein, the physical encodings encode information in the form of a code representing a number expressed in a numerical base (i.e., in this regard, the term "base" is used to refer to the number of complexity aspects of the encoding system) selected from the group consisting of bases 2, 3, 4, and higher bases, including without limitation bases 2-10.

Higher bases than base 4 may be used and the present invention is adaptable to higher base encoding strategies, especially as imaging resolutions, manufacturing methods, and software extraction methods improve. This permits a relatively detailed amount of information to be encoded into or onto the orientation marker rods while using a numeric base encoding system that may be discerned conveniently and accurately from outside the implanted patient through any imaging technique or system, such as through conventional medical imaging systems such as those described herein. For instance, where the orientation rods are inserted in the implant, the typical procedure using medical imaging as outlined in this application can be performed to read the encoded information. However, when the rod(s) is/are outside of the implant or in an implant that is transparent or provides some type of optical access, then visual inspection and/or a less enhanced optical imaging systems (such as normal vision system or camera) could be used to take a photograph of the rod(s) and determine the data encoded thereupon. In the manufacturing process, photographs may be used to track the encoded rods and ensure that the orientation rods are matched and inserted or associated with the appropriate implants. It will be understood that the present invention includes the manufacture of the data-encoded rods through the methods described herein, and the tracking of the encoded rods through the manufacture, shipping and/or installation process through any visual inspection and/or optical imaging systems that permit the encoded data to be read from the data-encoded rods.

In another variant embodiment of the invention described herein, each of the orientation marker rods has two longitudinally extending surfaces each having a respective series of physical encodings each so as to form respective two series of such physical encodings discernible by the imaging system, and wherein each of the respective series of such physical encodings encode respective first and second sets of data relating to the implant body. In one variant of this embodiment, each of the orientation marker rods defines a longitudinally extending dividing plane, and the two longitudinally extending surfaces of each of the orientation marker rods are disposed on opposite sides of that plane. In one variant of this embodiment, the orientation marker rods are disposed in the implant body such that an image of the two longitudinally extending surfaces of each of the orientation marker rods may be created from a single image taken from one direction with respect to the implant body. This may be achieved by positioning and aligning the orientation marker rods in the implant body such that the imaging vector avoids the rods eclipsing one another when imaged along a single imaging vector, and while the rods are aligned to permit contemporaneous and complete imaging of the encoded physical encodings in a single imaging view as exemplified herein.

In still another variant embodiment of the invention described herein, each of the series of notches or indentations or the like may be varied in depth (i.e., having more than one depth dimension without extending completely through the rod, especially where opposing sides of the rod are encoded); so to impart an additional numerical base, e.g., to raise the numerical base to a higher base, such as base 4 or beyond, which further increases the amount of information that may be encoded onto a given orientation marker rod.

Accordingly, the embodiments of the present invention may be such that the orientation marker rod(s) has/have physical encodings that comprise notches or indentations, and that the notches or indentations are placed on one, two or more discrete regions of at least one of said orientation marker rods, and that the notches or indentations are varied in at least two discrete predetermined depths, or varied in at least two discrete predetermined shapes, to increase the dimension(s) of the encoding protocol or system. In one such example, both sides of an orientation marker rod may be used to encode a first set of data (such as being encoded into both of a first set of two opposing sides of a square- or circular-cross-section orientation marker rod), and a second set of data may be encoded into one or both of a second set of two opposing sides of the same orientation marker rod (such as being encoded into one or both of a second set of two opposing sides of a square- or circular-cross-section orientation marker rod). This allows two sets of data to be obtained from respective different perspectives of a given orientation marker rod.

In yet another variant embodiment of the invention described herein, each of the series of notches or indentations or the like may be varied in geometry, such as by being of two or more of, for instance, semicircular, semi-ovoid, squared or triangonal, or any other imaging-discernable shape depending upon imager resolution, also to impart another numerical base dimension.

The present invention also includes a method of encoding data relating to an implant body into an implant body as described in its various embodiments herein, the method comprising: (a) obtaining an implant body; (b) preparing at least one orientation marker rod, each having a longitudinal extending surface having a series of physical encodings discernible by an imaging system, and wherein the physical encodings encode a respective set of data relating to the implant body; and (c) placing each of the orientation marker rods in the implant body. This may be done by using channels manufactured into the implant body for this purpose.

The number, region of placement and orientation of the orientation marker rods within the implant may be varied in accordance with application factors such as those described herein. For instance, the implant body may be viewed as defining at least two regions and having a channel in each of the regions, the channels may be arranged and oriented so as to bring about the desired relative orientation of the orientation marker rods. For instance, the channels may be distributed among several regions of the implant in order to place the orientation marker rods in a position and orientation to be conveniently and accurately imaged and the encoded data read therefrom. For instance, orientation marker rods may be arranged so as to be substantially parallel to one another, and arrayed so as to be individually discernable from the intended imaging vector(s).

The orientation marker rods may be of any material that is sufficiently visible through imaging to allow the encoded data to be appreciated therefrom and may depend upon the imaging system chosen. The materials from which the orientation marker rods may be made include metals, ceramics, polymeric materials (including those containing radiopaque materials), and the like, including any combination thereof.

Where the encoding is done through physical shaping of the orientation marker rods, the shaping may be done through any process and again may depend upon the encoding protocol chosen, as well as upon the imaging system resolution. The orientation marker rods may be machined, such as through micro-machining, wire electrical discharge machining (EDM), or impressed, embossed, molded, welded, any computer numerical controlled (CNC) machining, 5-axis lathe machining, or created through subtractive manufacturing or additive manufacturing, such as 3D printing.

The present invention also includes a method of obtaining data relating to an implant body, as described in its various embodiments herein, implanted in a patient, the method comprising: (a) bringing a patient into imaging proximity with an imaging system, the patient having implanted a spinal interbody implant comprising an implant body and comprising at least one orientation marker rod, each of the orientation marker rods having a longitudinal extending surface having a series of physical encodings discernible by an imaging system, and wherein the physical encodings encode a respective set of data relating to the implant body; and (b) imaging the orientation marker rod(s) so as to discern an image of the physical encodings; and (c) decoding the data from the image of the physical encodings.

The patient may be brought into imaging proximity with an imaging system in accordance with practices and procedures known and used in the art with respect to the imaging system chosen. It will be appreciated that the imaging approach and imaging angle may be varied in accordance with such factors as the orientation of the orientation marker rods within the implant, and the orientation of the implant within the patient, so as to permit the implant and the orientation marker rods to be imaged, and the encoded data relating to the implant body to be acquired.

As will be appreciated from the foregoing summary and exemplary embodiments, the imaging may be taken from any direction and along any vector, such as lateral or anterior-posterior (AP), as well as from multiple angles or an oblique angle, or from either end of any given implant or orientation marker rod (e.g., could be read top-bottom, bottom-top, or if symmetric, from either end).

The image decoding may be carried out through visual inspection, or by using software such as feature extraction or object identification algorithms from the subjects of image processing and/or computer vision adapted to extract the digital or numerical data from the image.

The methods of the present invention may be carried out in association with the use of spinal implants, including diagnostic, surgical and follow-up procedures, as well as procedures associated with medical research.

BRIEF DESCRIPTION OF THE FIGURES

While the specification concludes with claims particularly pointing out and distinctly claiming the present invention, it is believed that the present invention will be better understood from the following description in conjunction with the accompanying Drawing Figures, in which like reference numerals identify like elements, and wherein:

FIG. 11A is a photographic elevation view of an encoded orientation marker rod in accordance with further aspects of the present invention.

FIG. 11B is a photographic perspective view of a spinal interbody implant having an implant body and showing the placement apertures for an array of substantially parallel encoded orientation marker rods, in accordance with further aspects of the present invention.

FIG. 11C is an x-ray photographic perspective view of a spinal interbody implant having an implant body and showing the placement apertures for an array of substantially parallel encoded orientation marker rods, in accordance with further aspects of the present invention.

As used herein, reference to lateral, front or back sides is intended generically, and does not necessarily accord with the orientation of the implant within the body, which may vary in accordance with any given installation, as may be appreciated by one of ordinary skill in the art.

DETAILED DESCRIPTION

In the following detailed description of the preferred embodiment, reference is made to the accompanying drawings that form a part hereof, and in which is shown by way of illustration, and not by way of limitation, a specific preferred embodiment in which the invention may be practiced. It is to be understood that other embodiments may be utilized and that changes may be made without departing from the spirit and scope of the present invention.

Figure 1:
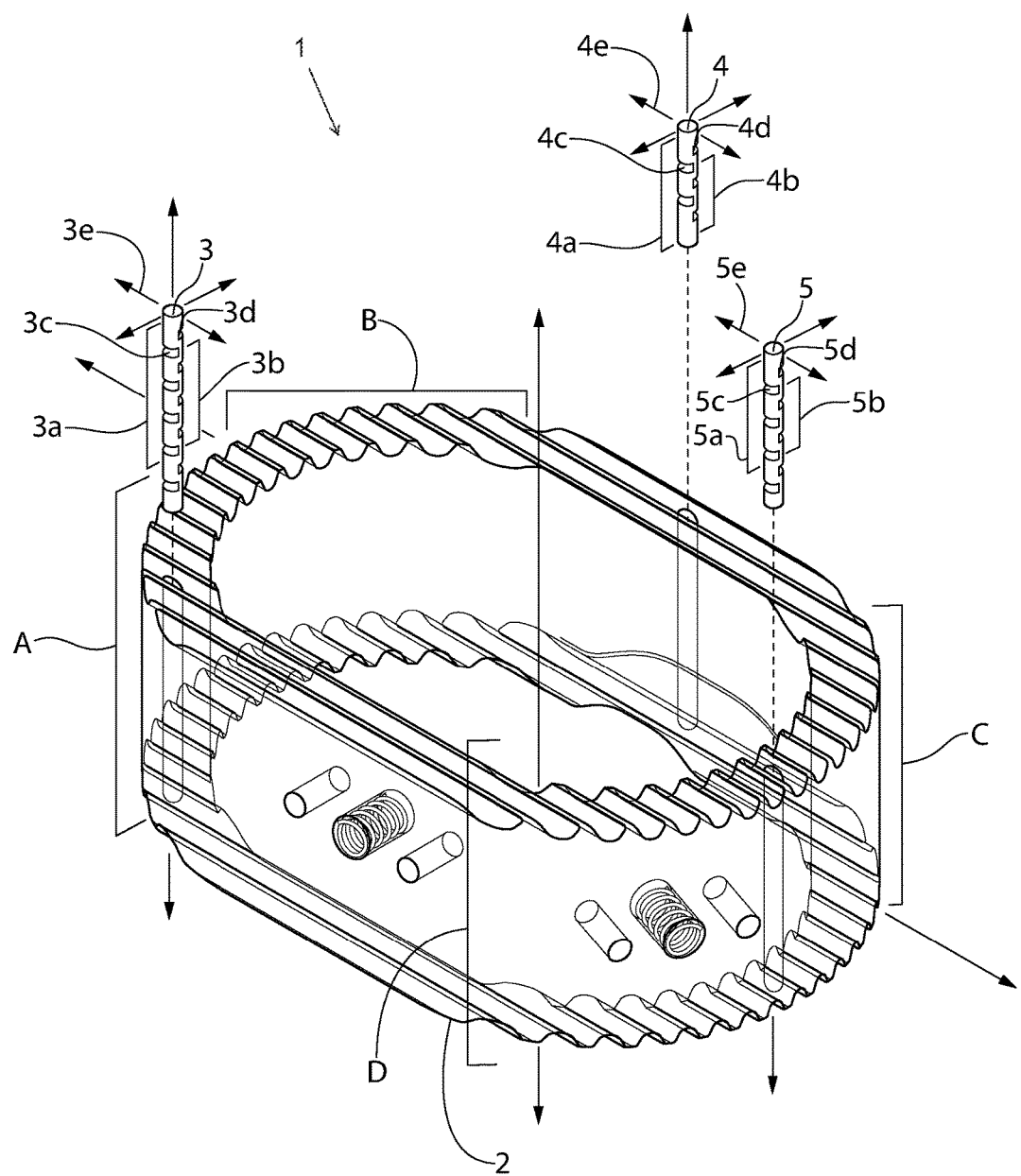
FIG. 1 is a isometric perspective, partially exploded view of an implant device identifiable and readable after implantation comprising a spinal interbody implant having an implant body and including an array of substantially parallel orientation marker rods, in accordance with aspects of the present invention.

Reference is now made to FIG. 1, which shows a spinal interbody implant 1 comprising an implant body 2, the implant body defining at least two regions (i.e., such as sectors A-D generally indicated in FIG. 1), and comprising an array of substantially parallel-oriented marker rods, such as marker rods 3, 4 and 5, placed in the displayed embodiment, such as, respectively, in sector A, in between B and C, and in between C and D.

Each of the orientation marker rods 3, 4 and 5, disposed in their respective regions, have a first longitudinally extending surface 3a, 4a and 5a, respectively. First longitudinally extending surfaces 3a, 4a and 5a each have a first series of notches or material indentations 3c, 4c and 5c, respectively, discernible by an imaging system, and wherein the notches or material indentations encode a respective first set of data relating to the implant body 2. In another embodiment, the orientation marker rods 3, 4 and 5 have second longitudinally extending surfaces 3b, 4b and 5b, each of which bear a respective second series of notches or material indentations 3d, 4d and 5d, likewise discernible by an imaging system. These notches or material indentations encode a respective second set of data relating to the implant body 2.

In one embodiment, all of the orientation marker rods 3, 4 and 5 are aligned such that the lines of separation of the longitudinally extending surfaces 3a, 4a and 5a from respective second longitudinally extending surfaces 3b, 4b and 5b are aligned such that the first series of notches or material indentations 3c, 4c and 5c and the second series of notches or material indentations 3d, 4d and 5d may be read by an imaging device or system viewing the orientation marker rods 3, 4 and 5 along a single vector, such as parallel to vectors 3e, 4e and 5e. In embodiments where two surfaces of multiple orientation marker rods are employed for encoded data, such alignment permits the data from both sides of each orientation marker rod to be obtained from a single image or measurement.

Figure 2:
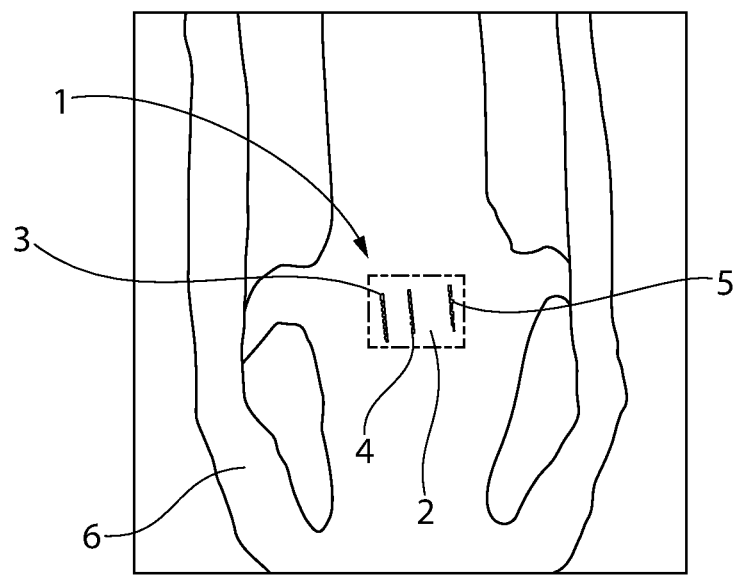
FIG. 2 is a lateral perspective imaging view (i.e., x-ray) of a spinal interbody implant having an implant body including an array of substantially parallel orientation marker rods, in accordance with aspects of the present invention.
Figure 2A:
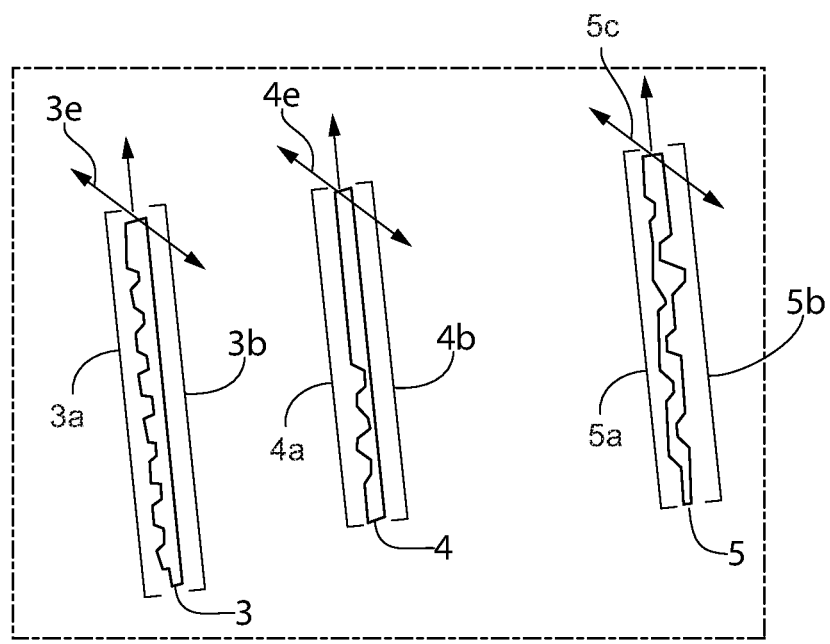
FIG. 2A is an extracted (i.e., objects identified with image processing algorithms) detailed view of the orientation marker rods, as they would appear and be oriented in a lateral perspective imaging view of an implant body, and allowing the encoded information to be obtained therefrom.

FIG. 2 shows a spinal interbody implant 1 comprising an implant body 2 as would appear in a patient 6 when viewed using an imaging device or system. FIG. 2A also shows an image extracted using image processing from the X-ray image in FIG. 2, and showing the orientation marker rods 3, 4 and 5 being aligned such that the lines of separation of the longitudinally extending surfaces 3a, 4a and 5a from respective second longitudinally extending surfaces 3b, 4b and 5b are aligned as described above.

Figure 3:
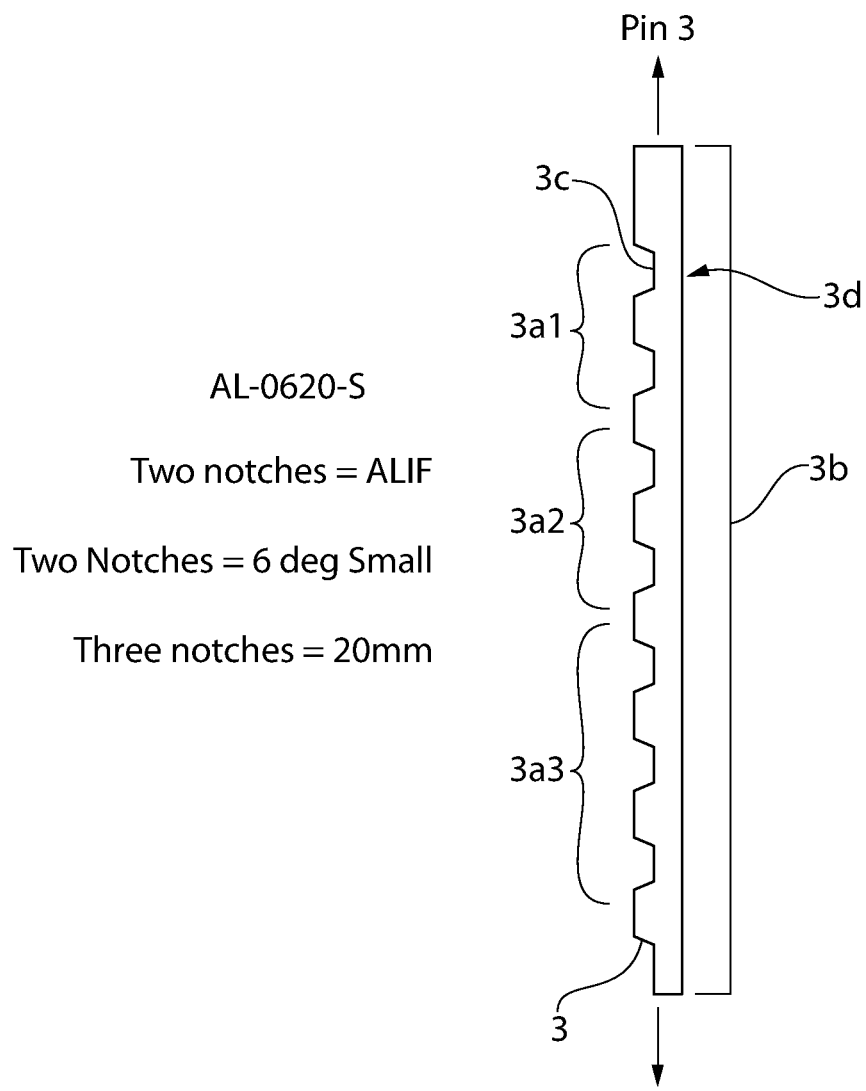
FIG. 3 is a view showing the encoding imparted to one of the orientation marker rods, as it would appear and be oriented in the lateral perspective imaging of an implant body, and describing the encoded respective information that may be obtained from regions thereof, in accordance with further aspects of the present invention.
Figure 4:
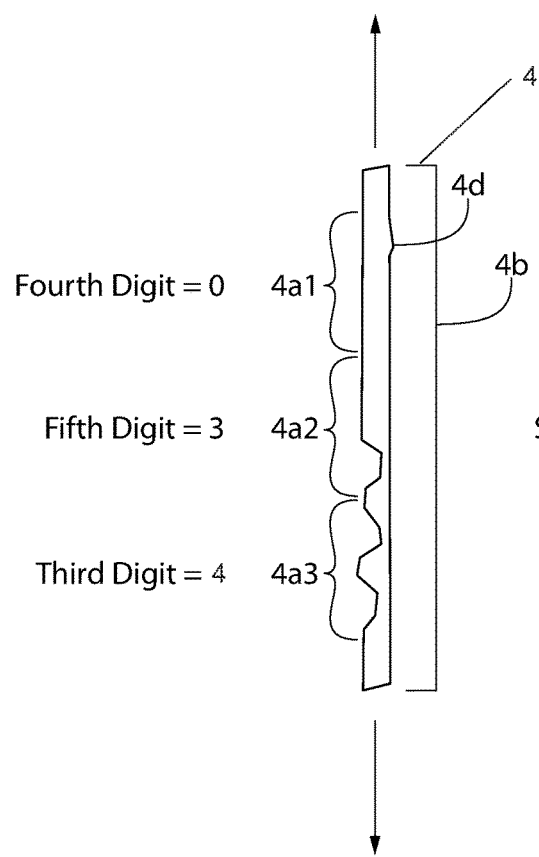
FIG. 4 is a view showing the encoding imparted to a second of the orientation marker rods, as it would appear and be oriented in the lateral perspective imaging of an implant body, and describing the encoded respective information that may be obtained from regions thereof in accordance with further aspects of the present invention.

FIG. 3 shows a detailed view of orientation marker rod 3, and further shows how, in one embodiment, the longitudinally extending surface 3a may be apportioned into multiple segments, such as segments 3a1, 3a2 and 3a3, to encode respective different discrete types or portions of data relating to spinal interbody implant 1 and/or the patient 6 and/or the patient's treatment. In the displayed embodiment, surface segment 3a1 is provided with notches or material indentations encoding the type of implant (i.e., ALIF), surface segment 3a2 is provided with notches or material indentations encoding the implant angle and size (i.e., 6 degree; small) and 3a3 is provided with notches or material indentations encoding some of the implant dimensions (i.e., 20 mm). Additional data may likewise be encoded into longitudinally extending surface 3b. FIG. 4 shows a detailed view of orientation marker rod 4, and further shows how, in one embodiment, the longitudinally extending surface 4a may be apportioned into multiple segments, such as segments 4a1, 4a2 and 4a3, to encode respective different discrete types or portions of data relating to spinal interbody implant 1 (such as all or a portion of the implant's numerical designation, such as its lot number (and/or serial number), such as in this case, the last three digits of 777034) and/or the patient 6 and/or the patient's treatment. In the displayed embodiment, surface segment 4*a*1 is provided with notches or material indentations encoding portions of the implant lot number (i.e., the numeral 0), surface segment 4*a*2 is provided with notches or material indentations encoding portions of the implant lot number (i.e., the numeral 3) and 4*a*3 is provided with notches or material indentations encoding portions of the implant lot number (i.e., the numeral 4). Additional data may likewise be encoded into longitudinally extending surface 4*b*.

Figure 5:
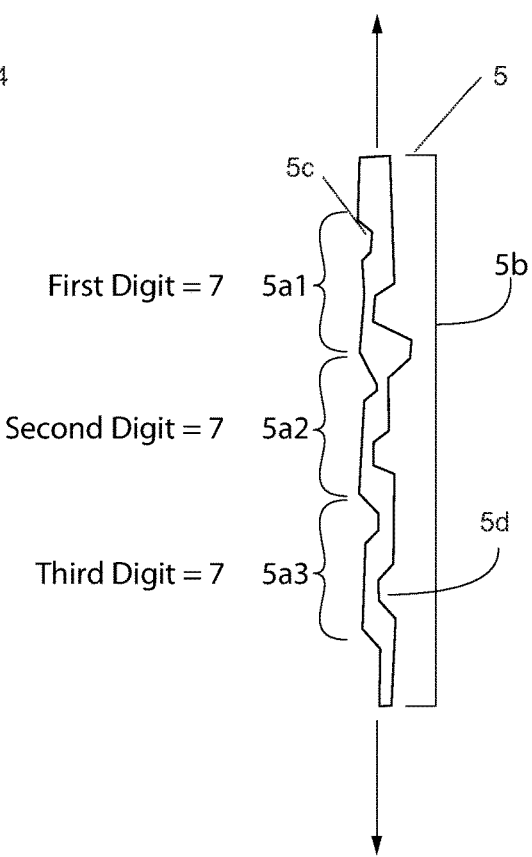
FIG. 5 is a lateral perspective view showing the encoding imparted to a third of the orientation marker rods, as it would appear and be oriented in the lateral perspective imaging of an implant body, and describing the encoded respective information that may be obtained from regions thereof in accordance with further aspects of the present invention.

FIG. 5 shows a detailed view of orientation marker rod 5, and further shows how, in one embodiment, the longitudinally extending surface 5*a* may be apportioned into multiple segments, such as segments 5*a*1, 5*a*2 and 5*a*3, to encode respective different discrete types or portions of data relating to spinal interbody implant 1 (such as all or a portion of the implant's lot number, such as in this case, the first three digits of 777034) and/or the patient 6 and/or the patient's treatment. In the displayed embodiment, surface segment 5*a*1 is provided with notches or material indentations encoding portions of the implant lot number (i.e., the numeral 7), surface segment 5*a*2 is provided with notches or material indentations encoding portions of the implant lot number (i.e., the numeral 7) and 5*a*3 is provided with notches or material indentations encoding portions of the implant lot number (i.e., the numeral 7). Additional data may likewise be encoded into longitudinally extending surface 5*b*.

FIGS. 4 and 5 thus also demonstrate some of the different discrete types or portions of data relating to spinal interbody implant 1 that may be apportioned over more than one of the orientation marker rods.

Figure 6:
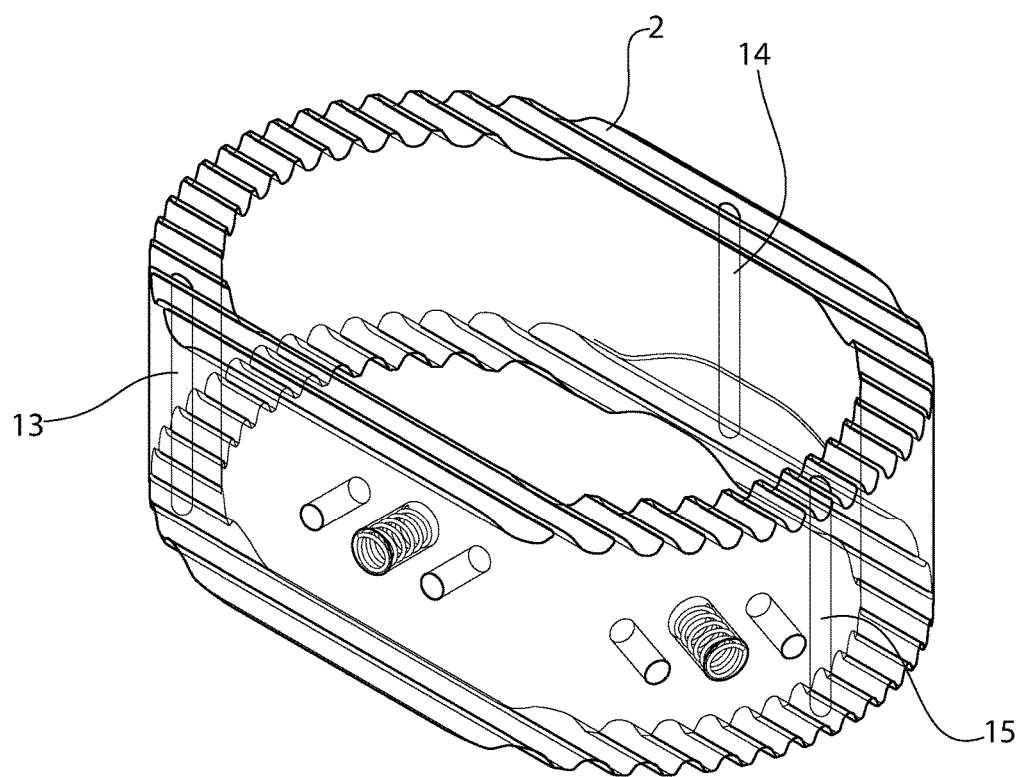
FIG. 6 is an isometric view of an implant device comprising a spinal interbody implant having an implant body and including an array of substantially parallel unencoded orientation marker rods.
Figure 7:
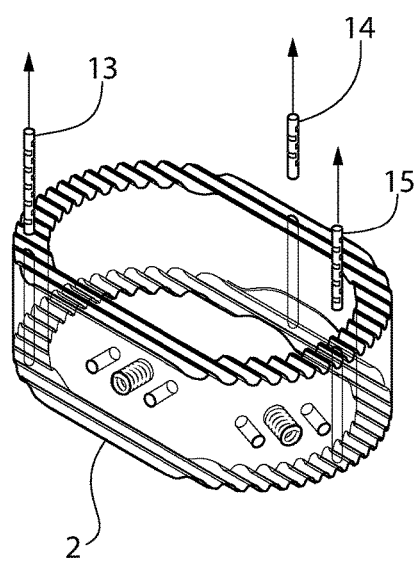
FIG. 7 is an isometric, partially exploded view of an implant device identifiable and readable after implantation comprising a spinal interbody implant having an implant body defining at least two regions and showing the removal of the array of substantially parallel unencoded orientation marker rods, in accordance with an optional step of the method of the invention.
Figure 7A:
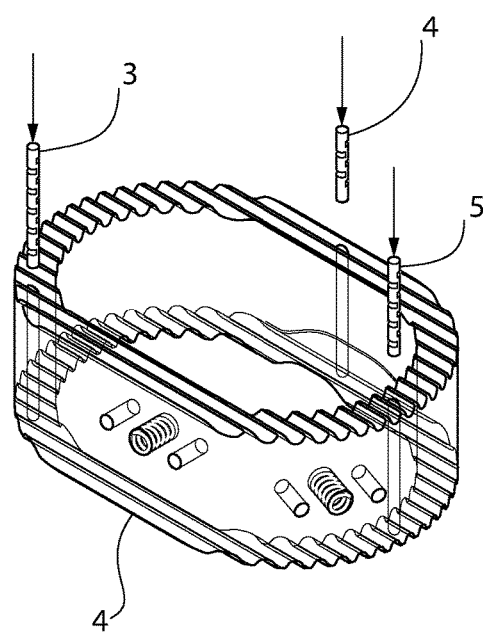
FIG. 7A is an isometric, partially exploded view of an implant device identifiable and readable after implantation comprising a spinal interbody implant having an implant body and showing the placement of the array of substantially parallel encoded orientation marker rods, in accordance with a method of the invention.

FIGS. 6, 7 and 7A show views of a progression of steps whereby a spinal interbody implant 1 may be obtained (FIG. 6), its original unencoded orientation marker rods 13, 14 and 15 removed (FIG. 7), and its unencoded orientation marker rods 13, 14 and 15 replaced by encoded orientation marker rods 3, 4 and 5.

Figure 8:
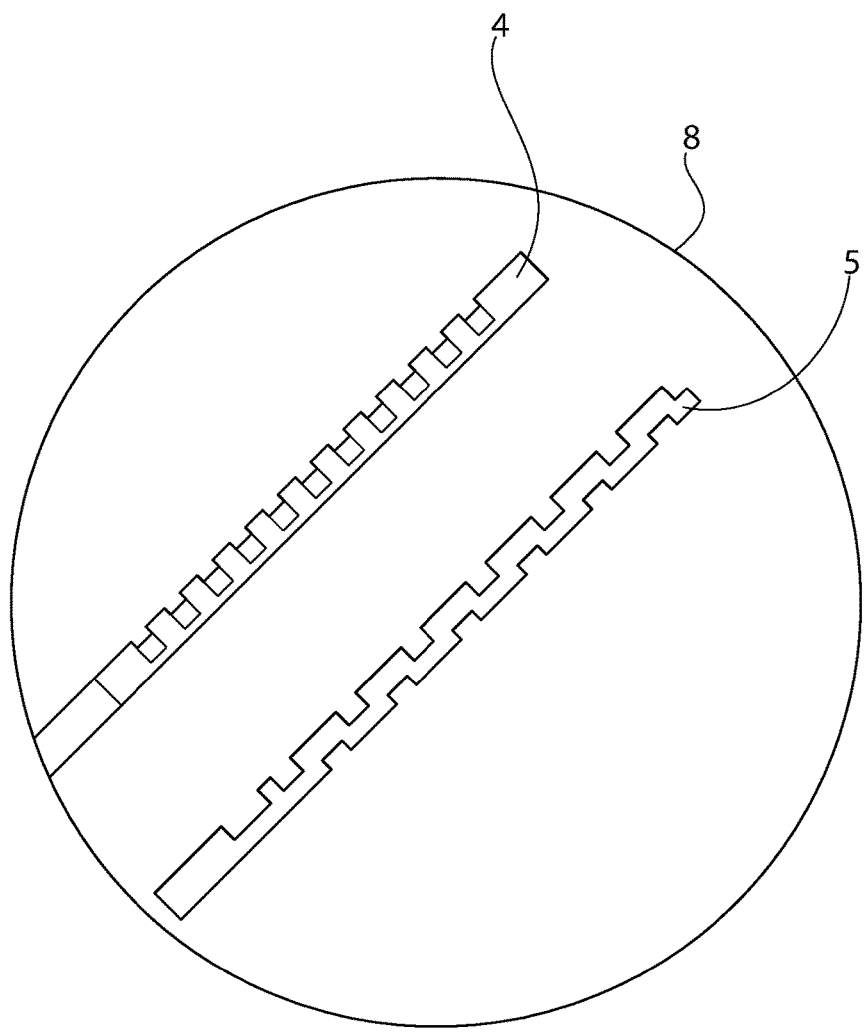
FIG. 8 is a photographic view of a packaged set of two encoded orientation marker rods, in accordance with further aspects of the present invention.

FIG. 8 is a detailed photographic image of encoded orientation marker rods 4 and 5 shown in a sterile package 8 that may be used in kit form to provide data relating to spinal interbody implant 1 (i.e., to provide the implant body 2 lot number) that may be delivered and/or assembled with the implant body 2 in advance of the placement surgical procedure.

Figure 9:
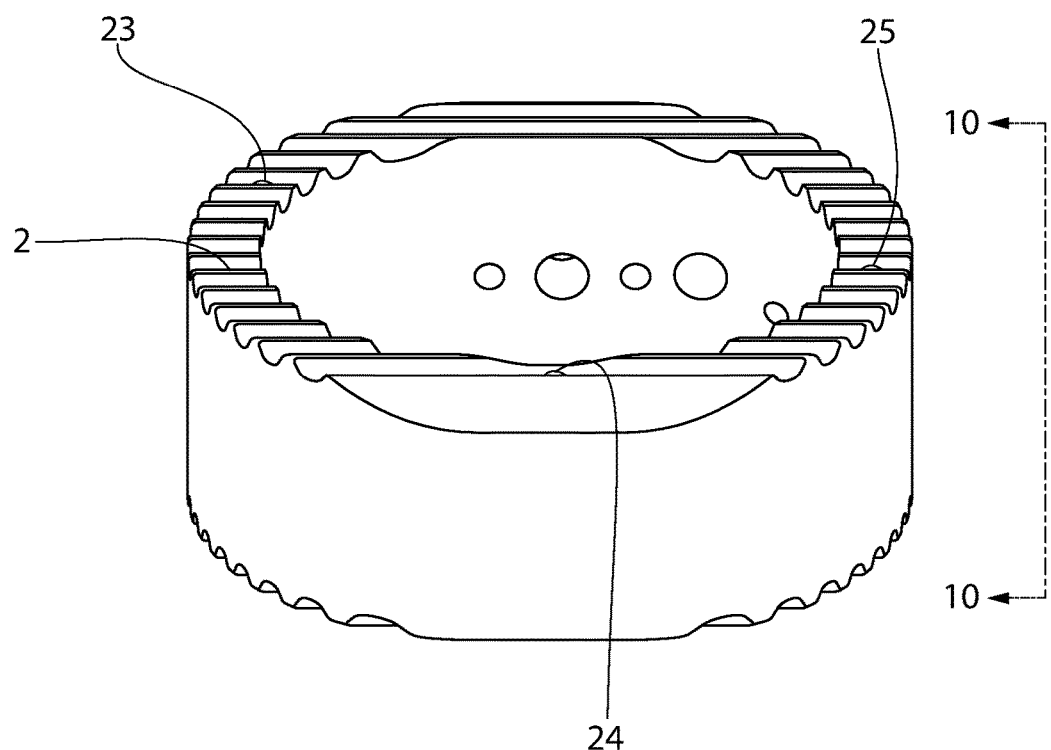
FIGS. 9 and 9A are respectively photographic and x-ray images of a frontal view (i.e., essentially an anterior-posterior view) of a spinal interbody implant having an implant body and showing the placement of the array of substantially parallel encoded orientation marker rods, in accordance with further aspects of the present invention.
Figure 9A:
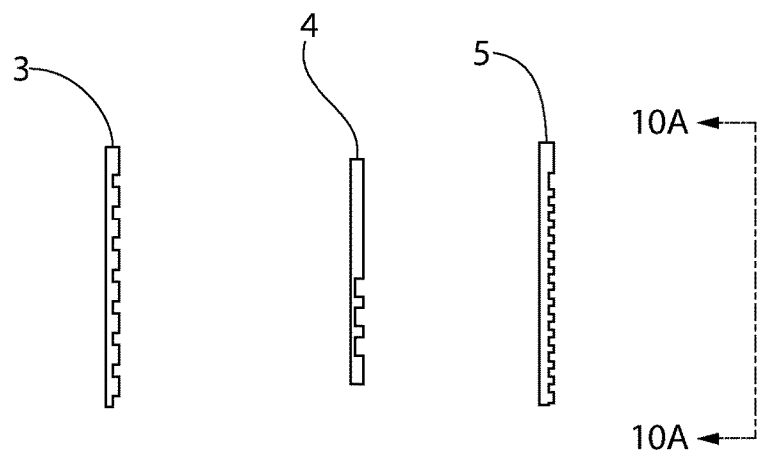

FIGS. 9 and 9A show respective detailed front view (i.e., typically anterior-posterior) and showing photographic and x-ray images of a frontal view of a spinal interbody implant 1 having an implant body 2 and showing the placement of the array of substantially parallel encoded orientation marker rods 3, 4 and 5.

Figure 10:
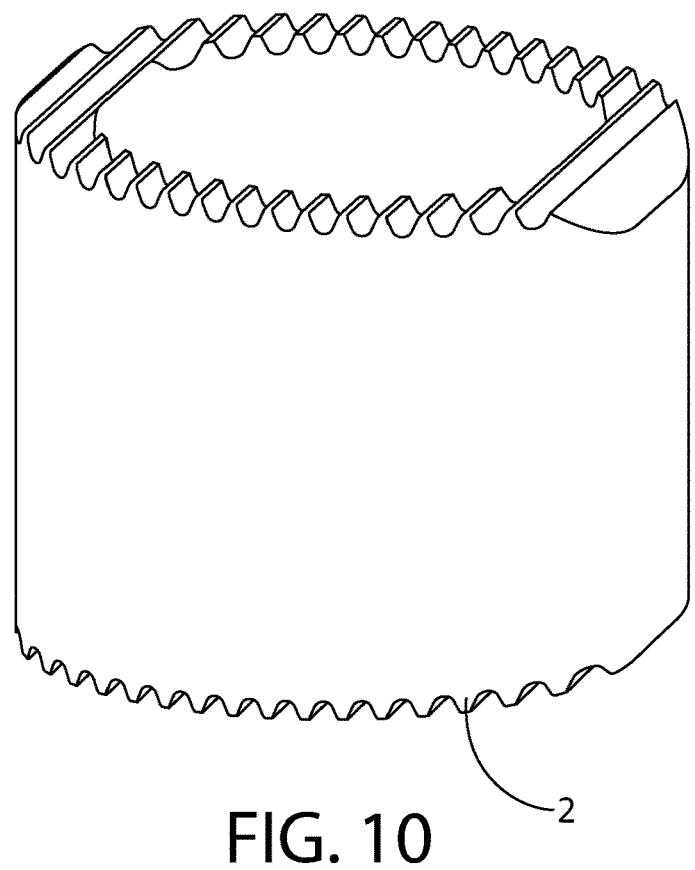
FIGS. 10 and 10A are respectively photographic and x-ray images of a lateral view of a spinal interbody implant having an implant body and showing the placement of the array of substantially parallel encoded orientation marker rods, in accordance with further aspects of the present invention.
Figure 10A:
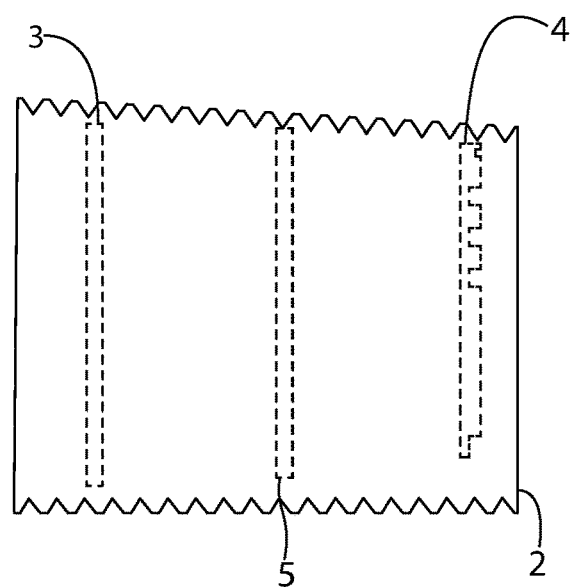

FIGS. 10 and 10A show respective detailed lateral views (as would typically be the lateral view in the body as normally implanted) and showing photographic and x-ray images of a lateral view of a spinal interbody implant 1 having an implant body 2 and showing the placement of the array of substantially parallel encoded orientation marker rods 3, 4 and 5. Comparing FIGS. 9 and 9A to FIGS. 10 and 10A, one can appreciate that for instance, some notches are visible on orientation rod 4 in the anterior-posterior view, while other notches on a different part of orientation rod 4 are visible in the perpendicular, lateral view, thus demonstrating that different portions or types of information can be encoded onto the orientation rods at different positions, and ultimately read from different imaging directions.

FIG. 11A is a photographic elevation view of an encoded orientation marker rod 5 showing its two longitudinally extending surfaces 5*a* and 5*b* having respective first and second series of notches or material indentations 5*c* and 5*d*. In this embodiment, the notches or material indentations may be approximately 0.3 mm in depth. Depth and distance between notches can be varied depending on the size of the rod, the associated manufacturing process, and imaging resolution available.

FIG. 11B is a photographic perspective view of a spinal interbody implant 1 having an implant body 2, and showing the placement apertures 23, 24 and 25 for the array of substantially parallel encoded orientation marker rods 3, 4 and 5.

FIG. 11C is an x-ray photographic image at 0.2 mm resolution showing a perspective view (i.e., the x-ray is a substantially AP (frontal) view of FIG. 11B, and being varied from the AP view by approximately 10-15 degrees) of a spinal interbody implant 1 having an implant body 2 and showing the placement of an array of substantially parallel encoded orientation marker rods 3, 4 and 5. This image shows the placement of encoded orientation marker rod 5 on FIG. 11A. In addition, in this embodiment, orientation marker rod 3 has respective first and second series of notches or material indentations 3*c* and 3*d* that may be approximately 0.5 mm in depth, while orientation marker rod 4 has respective first and second series of notches or material indentations 4*c* and 4*d* that may be approximately 0.25 mm in depth.

Figure 12:
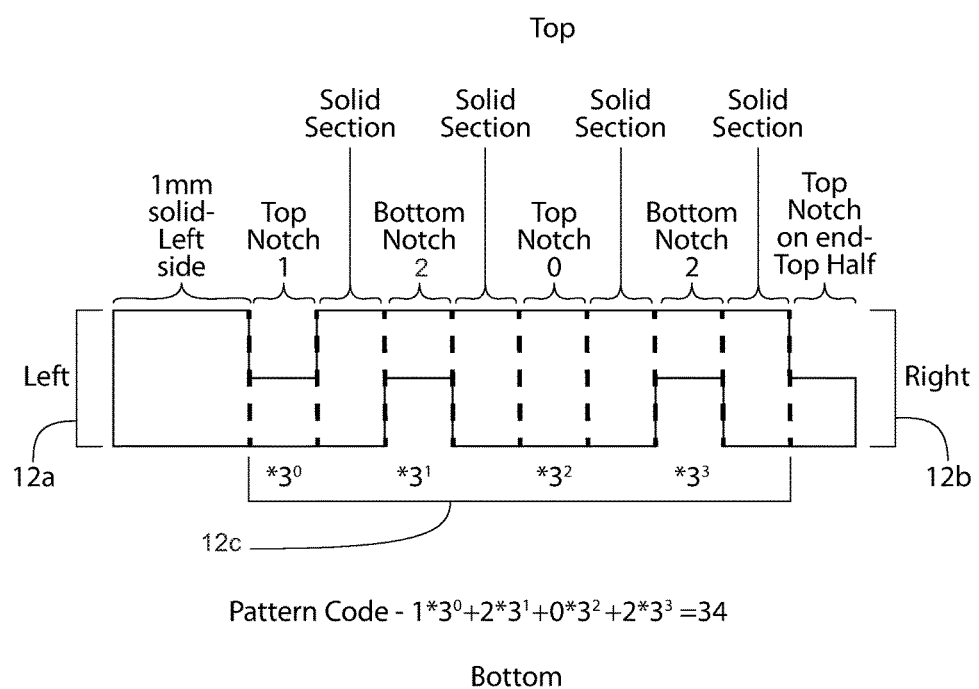
FIG. 12 is a schematic of an encoding strategy and protocol, using a base 3 number system, for an encoded orientation marker rod, in accordance with further aspects of the present invention.

FIG. 12 is a schematic of an encoding strategy and protocol, using a base 3 number system, for an encoded orientation marker rod. This figure shows that the notches or material indentations may be used in a coded pattern (read, for instance, from left to right) by applying a series of notches or material indentations, separated by unnotched/unindented sections, to identify, for instance, the left or right side of the implant body 2; i.e., through the use of a single notch or material indentation on one end (i.e., the right side 12*b*) while the left side 12*a* is identified by an initial unnotched/unindented section. In this embodiment, further notches or material indentations are provided in a central region 12*c*, and are separated by unnotched/unindented sections to provide a numerical code to result in a number 34, as shown in this figure. The notch at the bottom (i.e., shown on the right) of the rod in this embodiment is used to determine the bottom of the rod and thus its orientation for the purpose of data reading.

It will be appreciated that the notches or indentations may be off-axis with respect to the longitudinal axis of the rod while still allowing the data to be read.

Figure 13:
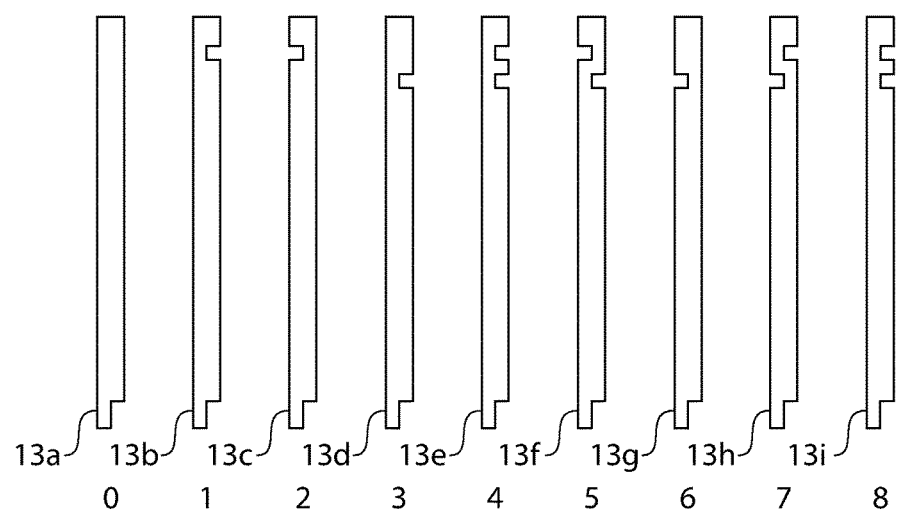
FIG. 13 is a schematic illustration of the encoding strategy and protocol demonstrating encoding numbers 0 through 8 (on individual rods) using the base 3 encoding strategy, in accordance with further aspects of the present invention.

FIG. 13 is a schematic illustration of the encoding strategy and protocol for using the base 3 strategy to encode the numbers 0 through 8 on individual rods, requiring two distinct locations of notches. FIG. 13 shows a series of nine encoded orientation marker rods 13*a*-13*i*, demonstrating an encoding wherein a relatively simple pattern or notches or material indentations, provided on different sides of the orientation rods, are employed to record data numerals. By so doing, encoded data may be imparted onto the implant body through its orientation rods which is readily visible to imaging devices and systems. It will be appreciated that, as shown in this example, the largest number that can be encoded on a single rod depends on the length of rod (i.e, the number of notches that can be included on the rod). The factors that influence how much information can be encoded on the rod include the type of encoding strategy employed (i.e., base 2, 3, 4, 5, 6, or more; typically bases 2-10), the notch type (such as cross-sectional geometry) and the width and/or depth of notches, the distance between notches, and the imaging resolution.

Figure 14:
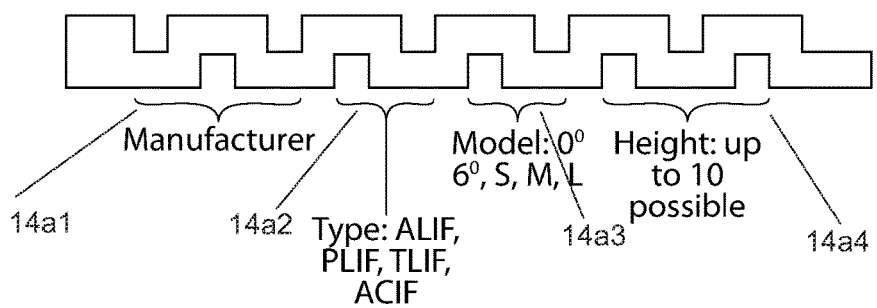
FIG. 14 is a schematic illustration of a first encoding scheme for a set of 3 encoded orientation marker rods whereby information in sets of notches is encoded, in accordance with further aspects of the present invention.
Figure 14:
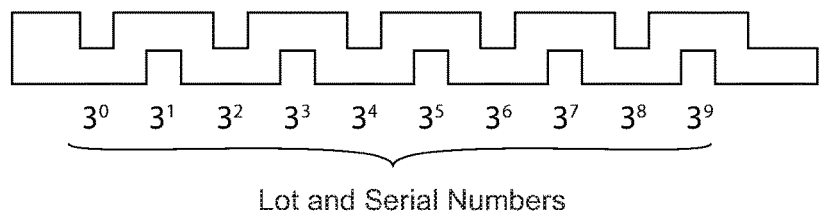

FIG. 14 is another schematic illustration of a first encoding scheme for a set of 3 encoded orientation marker rods (i.e., 14a, 14b and 14c) whereby information in sets of notches or material indentations is encoded. For instance segments 14a1, 14a2, 14a3 and 14a4 encode respective different discrete types or portions of data relating to spinal interbody implant, such as respectively the manufacturer, implant type (i.e., ALIF, PLIF, TLIF or ACIF), model designation (i.e., 0°, 6°, small, medium or large), and height (the implant height typically having 10 variations with the encoding region being able to express these heights by having at least 10 possible designations (i.e., encoding 10 possible designations within 27 discrete encoding possibilities; 3 levels and using base 3, should give 27 discrete encoding possibilities). In this embodiment, encoded orientation marker rods 14b and 14c are employed to encode, respectively the lot and serial numbers, such as by using a patterned code in accordance with a schematic of an encoding strategy and protocol such as shown in FIG. 12.

Figure 15:
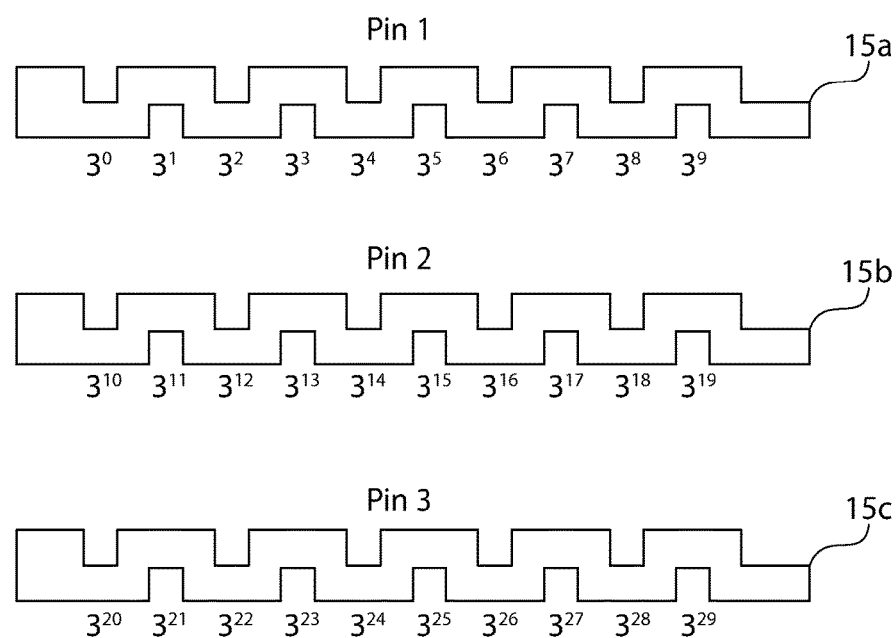
FIG. 15 is a schematic illustration of a second encoding scheme for a set of 3 encoded orientation marker rods whereby the implant's identifying number is encoded in sets of notches distributed among the orientation marker rods, in accordance with further aspects of the present invention.

FIG. 15 is a schematic illustration of a second encoding scheme for a set of 3 encoded orientation marker rods (i.e., 15a, 15b and 15c) whereby information in sets of notches or material indentations is encoded. For instance, orientation marker rods 15a, 15b and 15c encode respective different discrete portions of data relating to a spinal interbody implant, such as different portions of a given implant's identifying number, such as by using a patterned code in accordance with a schematic of an encoding strategy and protocol such as shown in FIG. 12. Another aspect of the subject encoding protocol is that one can encode a single unique number across as many rods as desired, to provide an additional level of encoding of, for instance, a given number or other data set, if desired.

Accordingly, this depicted strategy uses all available notch levels on all of the rods to devise a unique identifying number for the identified implant.

The strategy in FIG. 14 uses different regions of the rod to encode information such as manufacturer, type of implant, lot number and any combination of other information determined to be valuable or beneficial.

In still another variant of the invention, the encoding strategy or protocol may include the use of two or more discrete notch depths or notch shapes, to provide an additional dimension to the encoding. For instance, the notches in FIGS. 14 and 15 may be provided in two discrete notch depths, so as to raise the complexity of the encoding to one that utilizes a base 4 encoding protocol.

In another variant, further encoding complexity to add another dimension to the encoding may be realized through the use of discrete material types in different portions of the orientation rods. This may be accomplished for instance through the original manufacture of the orientation rods, such as by using different polymeric materials in discrete predetermined regions of a given orientation rod when molded, through the use of micro-welds with welding flux that varies in chemical composition, or through the use of any number of additive manufacturing techniques to impart different chemical, physical or chemico-physical properties to discrete predetermined regions of a given orientation rod. This material variation variant may be used with the other physical notch variations described above.

The encoding strategy could be each of these above or some combination of the two, or some other variant within the scope of this invention.

Figure 16:
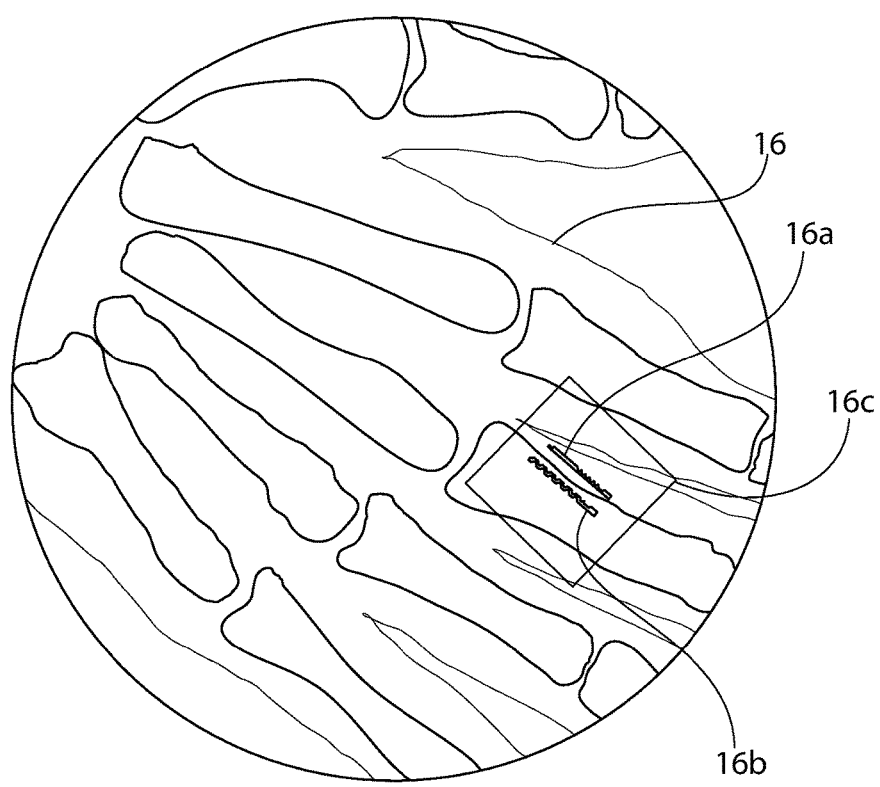
FIG. 16 is an x-ray photographic plan imaging view of a pair of substantially parallel encoded orientation marker rods as placed in an external measurement body attached in fixed relationship to a hand, the encoded rods having been imaged using a C-Arm imager, in accordance with further aspects of the present invention.

FIG. 16 is an x-ray photographic plan imaging view of a hand 16, and showing a pair of substantially parallel encoded orientation marker rods 16a and 16b as placed in a an external measurement body 16c adjacent a hand, the encoded rods having been imaged using a C-Arm imager, as yet another embodiment of the present invention. In this embodiment FIG. 16 shows an x-ray of a patient's hand placed over an external measurement body 16c (such as a piece of plastic or other relatively low radiopacity article to which the markers may be attached or embedded in a specific, prescribed orientation). The image shows the relative radiopacity of the markers relative to that of the bones and skin. An alternative imaging system could be used, such as by any method adapted to image the orientation marker rods and read the encoded data therefrom, such as through X-rays, CT scans, and other imaging modalities.

Figure 17:
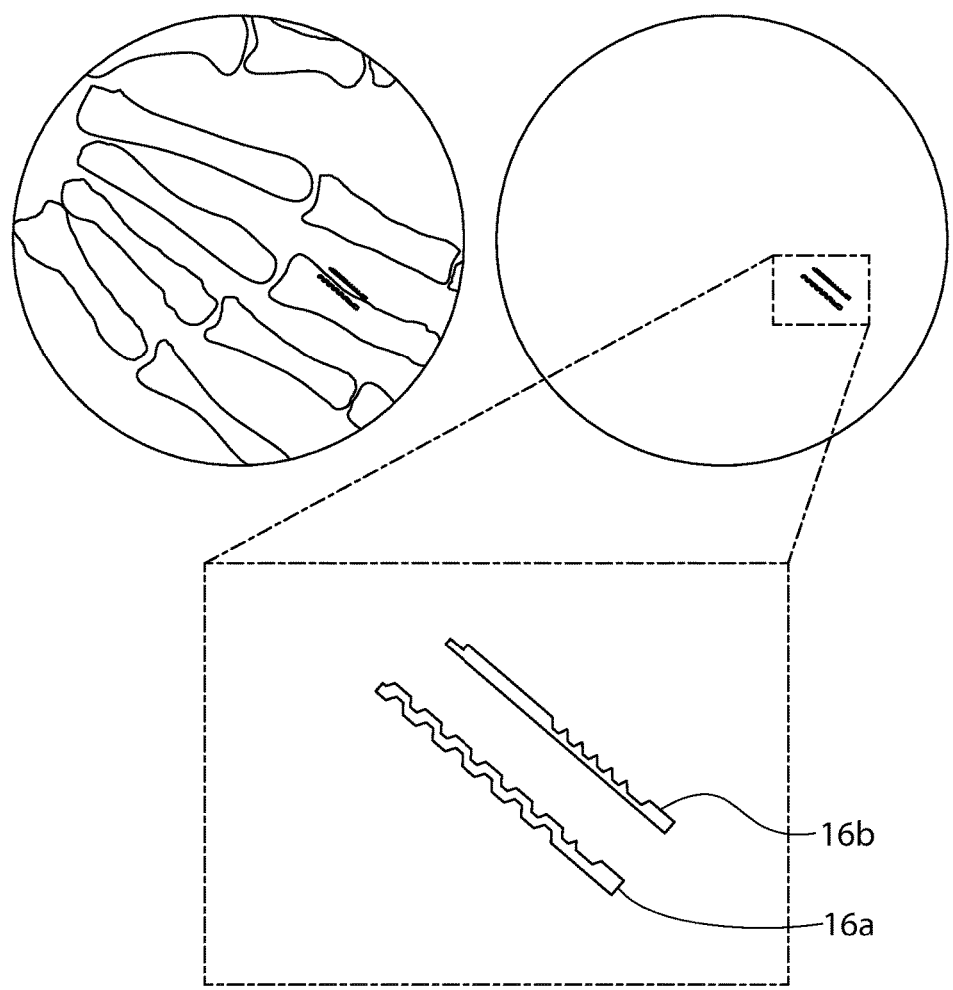
FIG. 17 is a detailed view of the x-ray photographic plan imaging view of FIG. 16, showing the pair of substantially parallel encoded orientation marker rods, as they would appear and be oriented, and as the encoded information may be obtained therefrom, in accordance with further aspects of the present invention.

FIG. 17 is a detailed view of the x-ray photographic plan imaging view of FIG. 16, showing the pair of substantially parallel encoded orientation marker rods 16a and 16b as placed in an external measurement body 16c adjacent a hand. This Figure shows the segmentation (through image processing) of the image of the orientation marker rods 16a and 16b from the balance of the x-ray photographic image, to permit the encoded information to be obtained therefrom, as described above. FIG. 17 shows on the right-side detailed view, the extracted rods using image processing of the x-ray image. Rods 16a and 16b in FIG. 17 are the image-extracted rods with the encoded information.

Figure 18A:
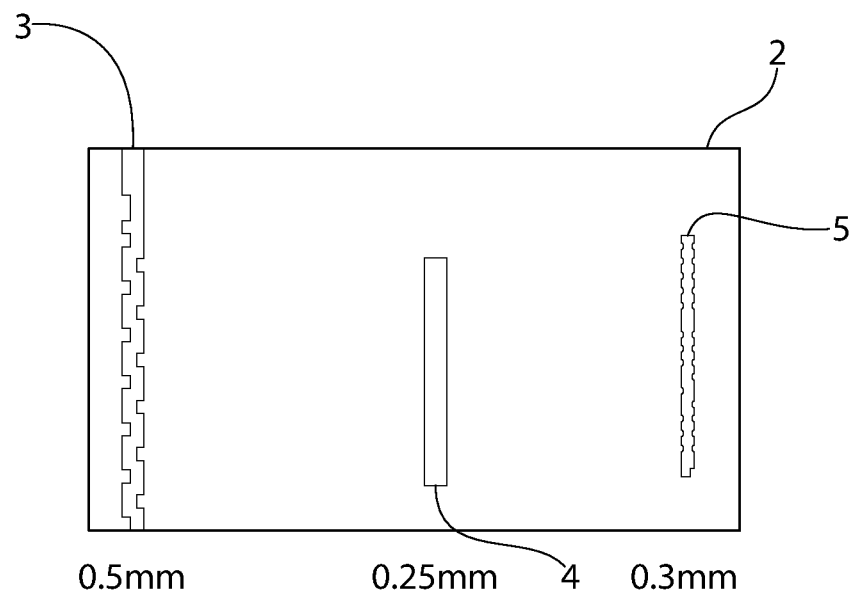
FIGS. 18A and 18B are respectively x-ray and extracted images (using image processing algorithms) of view (in this case slightly oblique to anterior-posterior view) of a spinal interbody implant having an implant body and showing the placement of the array of three substantially parallel encoded orientation marker rods, and comparing 0.5 mm, 0.3 mm, and 0.25 mm notches imaged at 0.2 mm, resolution in accordance with further aspects of the present invention.
Figure 18B:
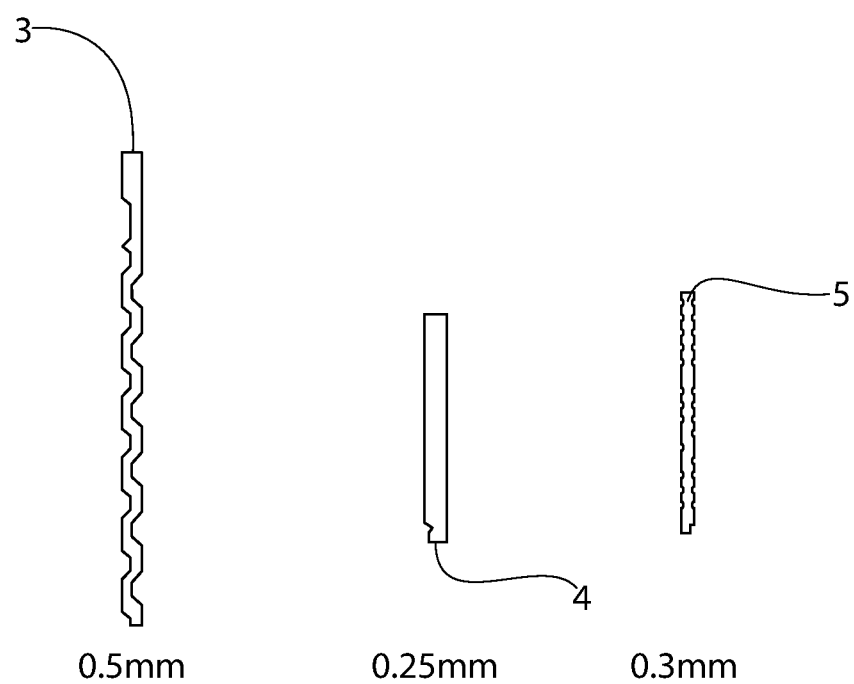

FIGS. 18A and 18B are respectively x-ray and schematic, extracted (i.e., image processed) images of a approximate AP view spinal interbody implant 1 having an implant body 2 (similar to that shown in FIG. 11C) and showing the placement of an array of substantially parallel encoded orientation marker rods 3, 4 and 5. FIG. 18B shows the segmentation of the image of the encoded orientation marker rods 3, 4 and 5 from the balance of the x-ray photographic image, to permit the encoded information to be obtained therefrom, as described above.

The method of the present invention may use any algorithm or software to extract the geometry of the orientation marker rods from the balance of the image. An experienced user of commercially available software (such as Mimics from Materialise of Plymouth, Mich.) in the method of the present invention may extract the image(s) of the orientation rods, and read their dimensionally encoded information from the image. Additionally, many private (Matlab) and open source (Open CV) software provide algorithms that may be adapted by an image processing software expert to extract the encoded information from the physically encoded object.

In addition, the dimensionally encoded information of the orientation rods likewise may be read before, during or after a surgical procedure to provide healthcare-related information to the healthcare provider. For instance, in the case of an implant procedure, the method of the present invention may be used to determine or discuss how the implant would be implanted, and, in surgery, the C-arm would take images and be processed. The invention may also include a method of tracking the actual implant in the patient and can track that implant over time (i.e., before, during, and after implantation), such as by using an X-ray image, CT image, or something similar.

Figure 19:
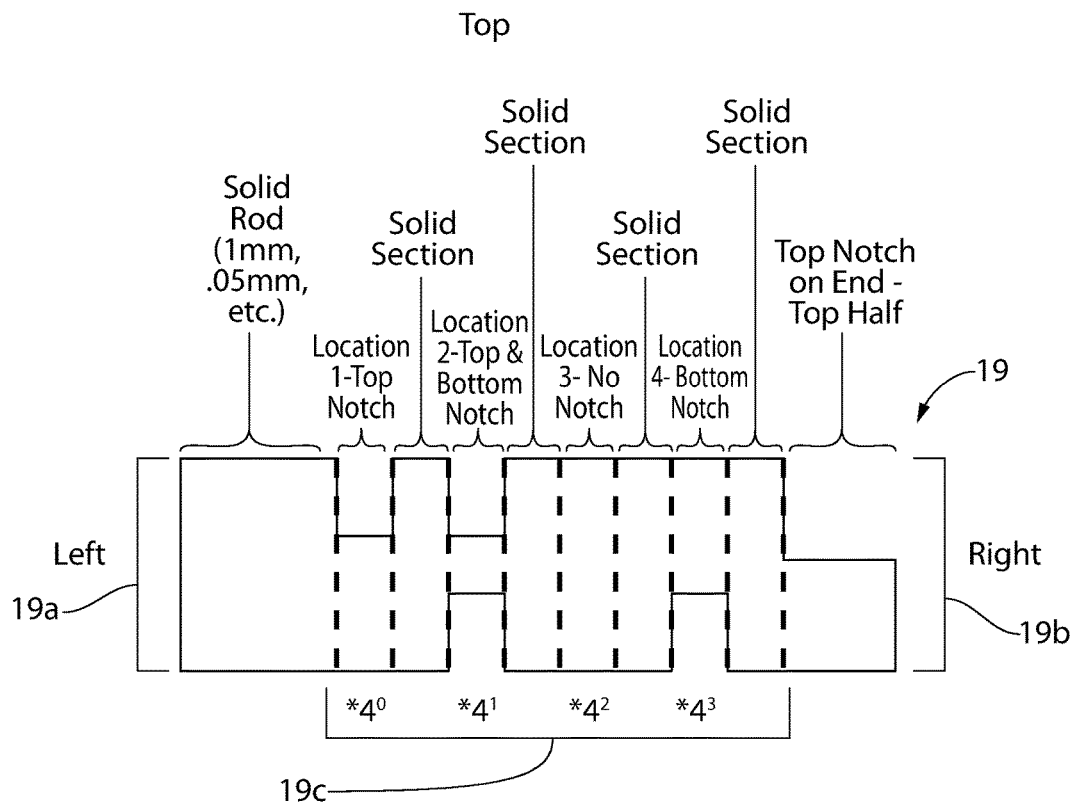
FIG. 19 is a schematic of an encoding strategy and protocol, using a first exemplary base 4 number system, for an encoded orientation marker rod, in accordance with further aspects of the present invention.

FIG. 19 is a schematic of an encoding strategy and protocol, using a first exemplary base 4 number system (i.e., using both sides of the orientation marker rod and the same depth of notches), for an encoded orientation marker rod 19. This figure shows that the notches or material indentations may be used in a coded pattern (read, for instance, from left to right) by applying a series of notches or material indentations, separated by unnotched/unindented sections, to identify, for instance, the left or right side of the implant body 19; i.e., through the use of a single notch or material indentation on one end (i.e., the right side 19*b*) while the left side 19*a* is identified by an initial unnotched/unindented section. In this embodiment, further notches or material indentations on both sides and at the same depth are provided in a central region 19*c*, and are separated by unnotched/unindented sections to provide a numerical code to result in a number 141, as shown in this figure. The notch at the top (i.e., shown on the right) of the rod in this embodiment is used to determine the top of the rod and thus its orientation for the purpose of data reading.

Figure 20:
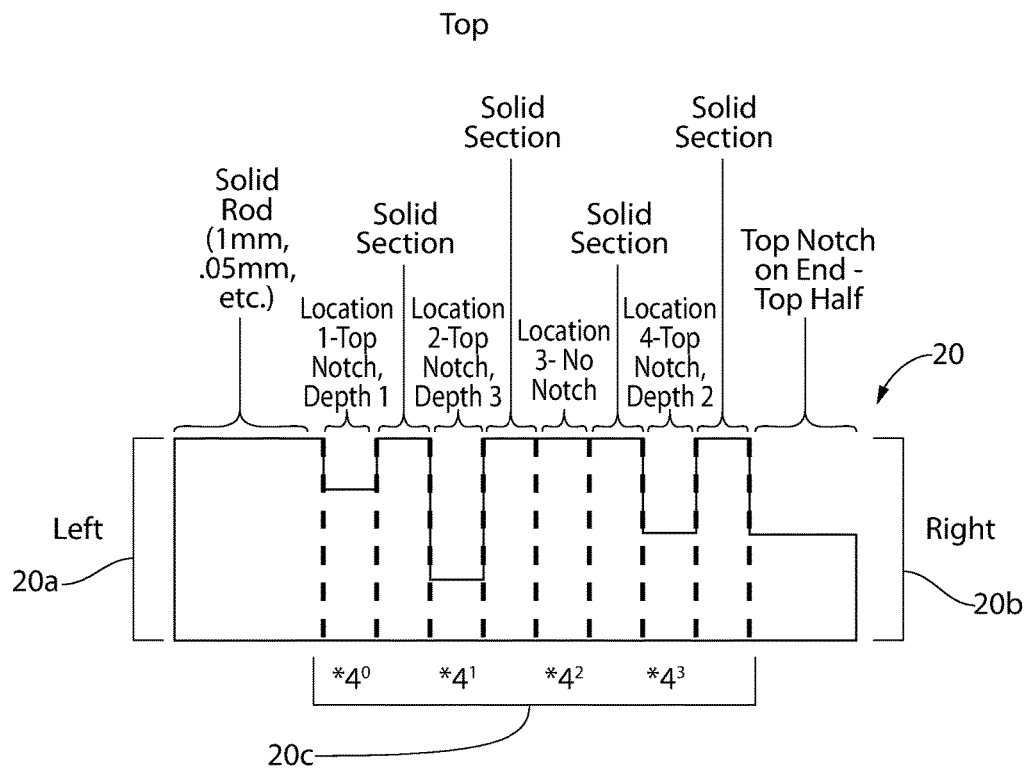
FIG. 20 is a schematic of an encoding strategy and protocol, using a second exemplary base 4 number system, for an encoded orientation marker rod, in accordance with further aspects of the present invention.

FIG. 20 is a schematic illustration of the encoding strategy and protocol for using the second exemplary base 4 number system (i.e., using one side of the orientation marker rod and three different depths of the notches), for an encoded orientation marker rod 20. This figure shows that the notches or material indentations may be used in a coded pattern (read, for instance, from left to right) by applying a series of notches or material indentations, separated by unnotched/unindented sections, to identify, for instance, the left or right side of the implant body 20; i.e., through the use of a single notch or material indentation on one end (i.e., the right side 20*b*) while the left side 20*a* is identified by an initial unnotched/unindented section. In this embodiment, further notches or material indentations on only one side, but at one or more of three prescribed depths are provided in a central region 20*c*, and are separated by unnotched/unindented sections to provide a numerical code to result in a number 141, as shown in this figure. The notch at the top (i.e., shown on the right) of the rod in this embodiment is used to determine the top of the rod and thus its orientation for the purpose of data reading.

Figure 21:
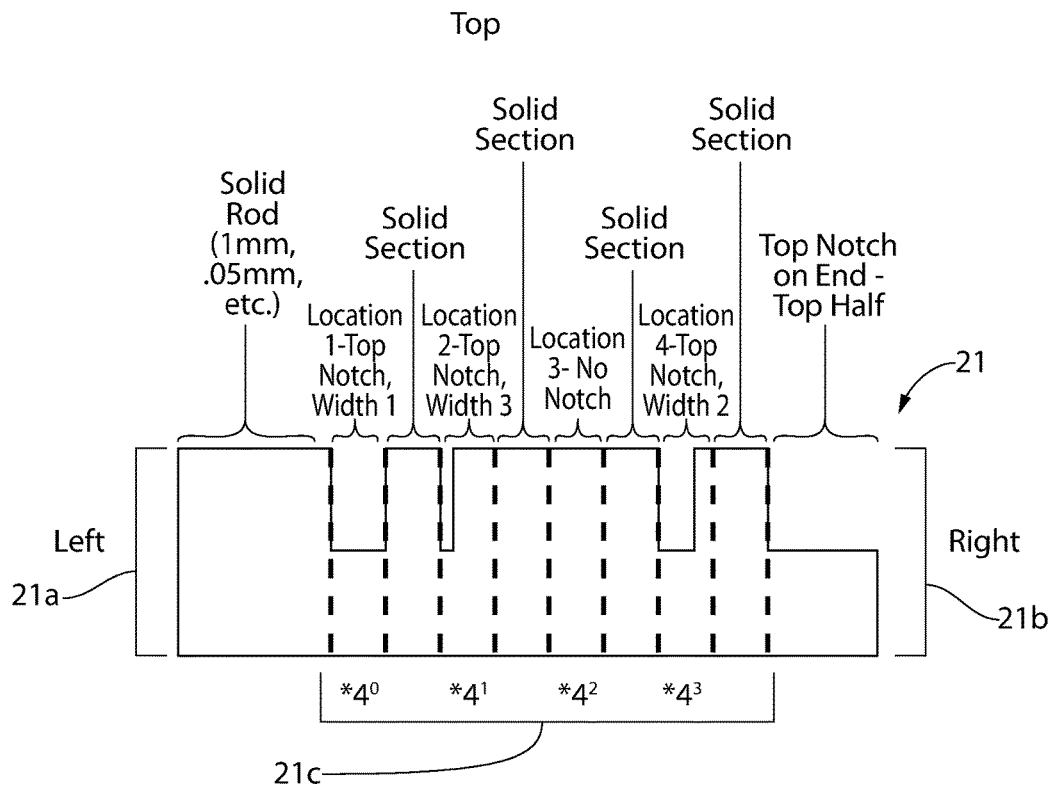
FIG. 21 is a schematic of an encoding strategy and protocol, using a third exemplary base 4 number system, for an encoded orientation marker rod, in accordance with further aspects of the present invention.

FIG. 21 is a schematic illustration of the encoding strategy and protocol for using the third exemplary base 4 number system (i.e., using one side of the orientation marker rod and three different widths of the notches), for an encoded orientation marker rod 21. This figure shows that the notches or material indentations may be used in a coded pattern (read, for instance, from left to right) by applying a series of notches or material indentations, separated by unnotched/unindented sections, to identify, for instance, the left or right side of the implant body 21; i.e., through the use of a single notch or material indentation on one end (i.e., the right side 21*b*) while the left side 21*a* is identified by an initial unnotched/unindented section. In this embodiment, further notches or material indentations on only one side, but in one or more of three prescribed widths are provided in a central region 21*c*, and are separated by unnotched/unindented sections to provide a numerical code to result in a number 141, as shown in this figure. The notch at the top (i.e., shown on the right) of the rod in this embodiment is used to determine the top of the rod and thus its orientation for the purpose of data reading.

Figure 22:
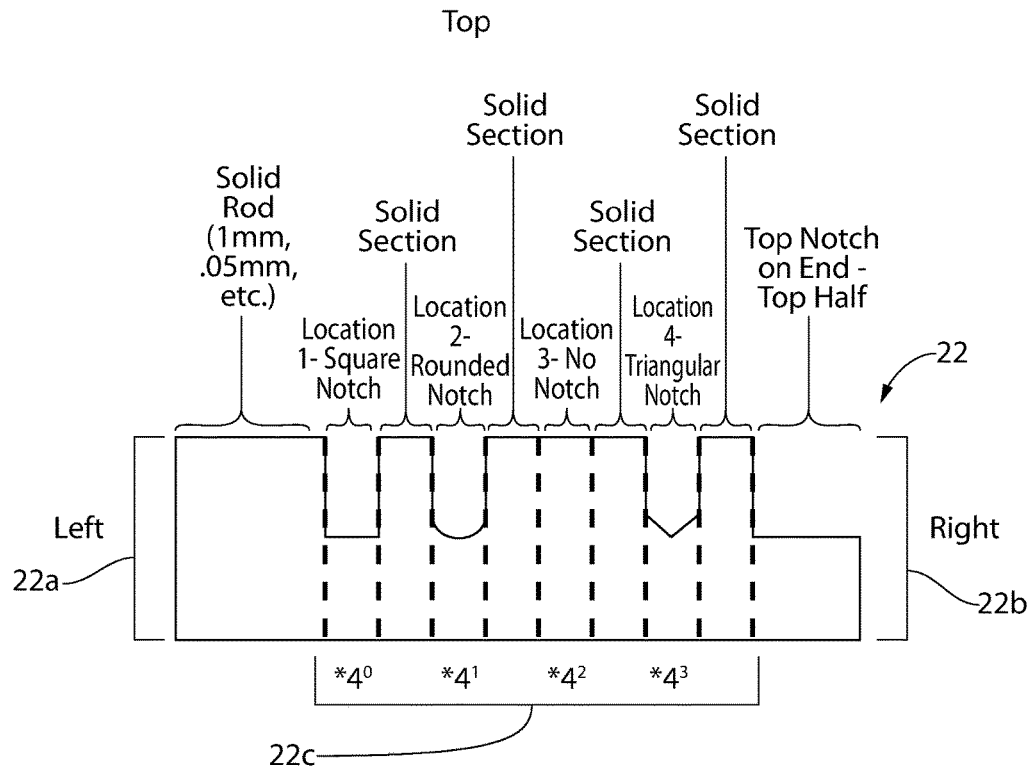
FIG. 22 is a schematic of an encoding strategy and protocol, using a fourth exemplary base 4 number system, for an encoded orientation marker rod, in accordance with further aspects of the present invention.

FIG. 22 is a schematic illustration of the encoding strategy and protocol for using the fourth exemplary base 4 number system (i.e., using one side of the orientation marker rod and three different shapes or geometries of the notches), for an encoded orientation marker rod 22. This figure shows that the notches or material indentations may be used in a coded pattern (read, for instance, from left to right) by applying a series of notches or material indentations, separated by unnotched/unindented sections, to identify, for instance, the left or right side of the implant body 22; i.e., through the use of a single notch or material indentation on one end (i.e., the right side 22*b*) while the left side 22*a* is identified by an initial unnotched/unindented section. In this embodiment, further notches or material indentations on only one side, but in one or more of three prescribed shapes or geometries are provided in a central region 22*c*, and are separated by unnotched/unindented sections to provide a numerical code to result in a number 141, as shown in this figure. The notch at the top (i.e., shown on the right) of the rod in this embodiment is used to determine the top of the rod and thus its orientation for the purpose of data reading.

Figure 23:
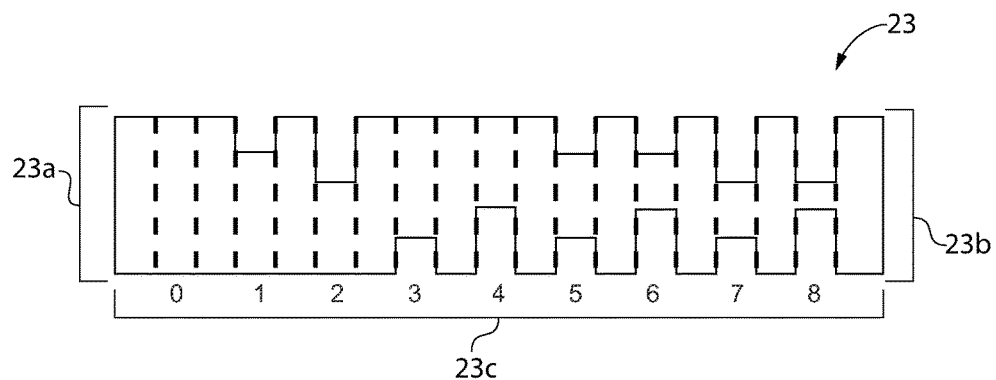
FIG. 23 is a schematic of an encoding strategy and protocol, using an exemplary base 9 number system, for an encoded orientation marker rod, in accordance with further aspects of the present invention.

FIG. 23 is a schematic illustration of the encoding strategy and protocol for using an exemplary base 9 number system (i.e., using both sides of the orientation marker rod and two prescribed depths of notches), for an encoded orientation marker rod 23. This figure shows that the notches or material indentations may be used in a coded pattern (read, for instance, from left to right) by applying a series of notches or material indentations, separated by unnotched/unindented sections, to identify, for instance, the left or right side of the implant body 23; i.e., through the use of a single notch or material indentation on one end (not shown) (i.e., the right side 23*b*) while the left side 23*a* is identified by an initial unnotched/unindented section. In this embodiment, further notches or material indentations on both sides, and in one or more of three prescribed depths are provided in a central region 22*c*, and are separated by unnotched/unindented sections to provide a numerical code to result in a number 141, as shown in this figure. The notch at the top (i.e., shown on the right) of the rod in this embodiment is used to determine the top of the rod and thus its orientation for the purpose of data reading.

Accordingly, these strategies may use available notch depths, position and/or shapes on all of the rods to devise a unique identifying number for the identified implant, to encode information such as manufacturer, type of implant, lot number and any combination of other information determined to be valuable or beneficial.

In still another variant of the invention, the encoding strategy or protocol may include the use of two or more discrete notch depths or notch shapes, to provide an additional dimension to the encoding. In another variant, further encoding complexity to add another dimension to the encoding may be realized through the use of discrete material types in different portions of the orientation rods. This may be accomplished for instance through the original manufacture of the orientation rods, such as by using different polymeric materials in discrete predetermined regions of a given orientation rod when molded, through the use of micro-welds with welding flux that varies in chemical composition, or through the use of any number of additive manufacturing techniques to impart different chemical, physical or chemico-physical properties to discrete predetermined regions of a given orientation rod. This material variation variant may be used with the other physical notch variations described above.

The encoding strategy could be each of these above or some combination of the two, or some other variant within the scope of this invention.

While particular embodiments of the present invention have been illustrated and described, it would be obvious to those skilled in the art that various other changes and modifications can be made without departing from the spirit and scope of the invention. It is therefore intended to cover in the appended claims, which themselves constitute part of the disclosure, all such changes and modifications that are within the scope of this invention.

What is claimed is:

1. An implant device identifiable after implantation comprising:
a spinal interbody implant comprising an implant body comprising at least one orientation marker rod having a first and a second longitudinally extending surface, wherein the first longitudinally extending surface is comprised of a first series of encodings representing a first data set and the second longitudinally extending surface is comprised of a second series of encodings representing a second data set, and further wherein said first and second series of encodings are discernable by an imaging system.

2. The implant device of claim 1, wherein said imaging system is of a type selected from the group consisting of at least one of x-ray, fluoroscopy, computed tomography, electromagnetic radiation, ultrasound, positron emission tomography (PET), and magnetic resonance imaging.

3. The implant device of claim 1, wherein each of said at least one orientation marker rod has physical encodings that encode respective different sets of data relating to said implant body.

4. The implant device of claim 1, wherein each of said at least one orientation marker rod has physical encodings that respectively encode at least two sets of data relating to said implant body.

5. The implant device of claim 1, wherein each of said first and second data sets relate to said implant body and is selected from the group consisting of implant type, implant manufacturer identification, implant serial number, implant type and size, implant lot number, a unique device identifier (UDI), data relating to the FDA Global Unique Device Identification Database (GUDID), and the FDA UDI.

6. The implant device of claim 1, wherein each of said first and second series of encodings encode information in the form of a code representing a number expressed in a numerical base selected from the group consisting of bases 2-10.

7. An implant device identifiable after implantation comprising:
a spinal interbody implant comprising an implant body comprising an orientation marker rod having a longitudinally extending dividing plane and two longitudinally extending surfaces each having a respective series of physical encodings thereon that are discernible by an imaging system, and further wherein a first of said two longitudinally extending surfaces is disposed on a first side of said longitudinally extending dividing plane and a second of said two longitudinally extending surfaces is disposed on an opposite side of said longitudinally extending dividing plane.

8. The implant device of claim 7, wherein said imaging system is of a type selected from the group consisting of at least one of x-ray, fluoroscopy, computed tomography, electromagnetic radiation, ultrasound, positron emission tomography (PET), and magnetic resonance imaging.

9. The implant device of claim 7, wherein each of said respective series of such physical encodings encode respective first and second sets of data relating to said implant body, and further wherein said first and second sets of are selected from the group consisting of implant type, implant manufacturer identification, implant serial number, implant type and size, implant lot number, a unique device identifier (UDI), data relating to the FDA Global Unique Device Identification Database (GUDID), and the FDA UDI.

10. The implant device of claim 7, wherein said physical encodings encode information in the form of a code representing a number expressed in a numerical base selected from the group consisting of bases 2-10.

11. The implant device of claim 7, wherein said orientation marker rod is disposed in said implant body such that an image of said two longitudinally extending surfaces may be created from a single image taken from one direction with respect to said implant body.

12. The implant device of claim 7, wherein said implant device has at least two orientation marker rods, and further wherein each of said at least two orientation marker rods has physical encodings that comprise notches or indentations.

13. The implant device of claim 12, wherein said notches or indentations are placed on two discrete regions of at least one of said at least two orientation marker rods.

14. The implant device of claim 13, wherein said notches or indentations are placed on both a first and a second discrete regions of at least one of said at least two orientation marker rods, and wherein at least two of said notches or indentations vary in depths.

15. The implant device of claim 13, wherein said notches or indentations are placed on both a first and a second discrete regions of at least one of said at least two orientation marker rods, and wherein at least two of said notches or indentations vary in shape.

16. An implant device identifiable after implantation comprising: a spinal interbody implant comprising an implant body defining at least two regions and comprising a plurality of substantially parallel orientation marker rods, at least one of said plurality of orientation marker rods disposed in each of said at least two regions and having two longitudinally extending surfaces each having a respective series of physical encodings thereon discernible by an imaging system, and further wherein each of said respective series of physical encodings encode respective first and second sets of data relating to said implant body.

17. The implant device of claim 16, wherein said imaging system is of a type selected from the group consisting of at least one of x-ray, fluoroscopy, computed tomography, electromagnetic radiation, ultrasound, positron emission tomography (PET), and magnetic resonance imaging.

18. The implant device of claim 16, wherein each of said first and second sets of data relating to said implant body is selected from the group consisting of implant type, implant manufacturer identification, implant serial number, implant type and size, implant lot number, a unique device identifier (UDI), data relating to the FDA Global Unique Device Identification Database (GUDID), and the FDA UDI.

19. The implant device of claim 16, wherein said physical encodings encode information in the form of a code representing a number expressed in a numerical base selected from the group consisting of bases 2-10.

* * * * *